United States Patent [19]

Baikoff

[11] Patent Number: 5,071,432
[45] Date of Patent: Dec. 10, 1991

[54] ANTERIOR CHAMBER INTRAOCULAR IMPLANT

[75] Inventor: Georges Baikoff, Corniche, France

[73] Assignee: Laboratoires Domilens, Lyons, France

[21] Appl. No.: 350,377

[22] Filed: May 11, 1989

[30] Foreign Application Priority Data

May 11, 1988 [FR] France .................. 88 07042

[51] Int. Cl.⁵ .............................................. A61F 2/16
[52] U.S. Cl. ..................................................... 623/6
[58] Field of Search ........................................... 623/6

[56] References Cited

U.S. PATENT DOCUMENTS

| 2,834,023 | 5/1958 | Lieb | 623/6 |
| 4,504,981 | 3/1987 | Walman | 623/6 |
| 4,642,113 | 2/1987 | Dubnoff | 623/6 |
| 4,676,792 | 6/1987 | Praeger | 623/6 |

FOREIGN PATENT DOCUMENTS

| 0195881 | 10/1986 | European Pat. Off. | 623/6 |
| 0215468 | 3/1987 | European Pat. Off. | 623/6 |

OTHER PUBLICATIONS

"Lens Styles from Cilco", Brochure from Cilco, 6 pages, Oct. 1982, pp. 1, 2 and 6 cited. Lens Styles MT-3-MT-7, relied upon on p. 2, 623-6.

Anterior Chamber and/or Posterior Chamber Model 120 Feaster Dualens (advertisement page), Coburn Professional Products Div., P.O. Box 2498, Clearwater, FL 33517, Aug. 1983, 623-6.

Primary Examiner—Ronald Frinks
Attorney, Agent, or Firm—Browdy and Neimark

[57] ABSTRACT

The present invention relates to the intraocular implant (13) for the anterior chamber of the eye.

The implant comprises an optic part comprising essentially a divergent lens with thick edges (16), and a haptic part comprising two elastic loops (15) for support inside the eye, extending on either side of the optic part, in the same diametral direction (50), from two points of the optic part respectively and diametrically opposed. A connecting zone (19) situated outside the optic part and fitted on each loop (15) connects the latter to the optic part.

The invention is applicable to the correction of myopias.

9 Claims, 2 Drawing Sheets

ANTERIOR CHAMBER INTRAOCULAR IMPLANT

FIELD OF THE INVENTION

The present invention relates to an anterior chamber intraocular implant intended to correct optic myopias, and this by surgical operation on the eye.

PRIOR ART

In Patent Application EP-A-0,195,881 an implant is described and proposed which consists of:

an optic part, that is to say a part deflecting the light rays issued from the cornea towards the pupil; this optic part comprises, centrally and axially, a convergent biconvex lens of essentially circular shape and, on its periphery, two diametrically opposed joining zones with two respective loops for elastic support, defined hereinafter:

a haptic part, that is to say a part playing no useful optic rôle vis-á-vis the light rays received by the cornea; this haptic part comprises two elastic loops for elastic support inside the eye and whose thickness is relatively slight compared to the axial thickness of the lens; these two loops extend on either side of the optic part, in the same diametral direction, from the two joining zones respectively of the optic part.

Such an implant is intended to be arranged in front of the iris inside the eye, in accordance with FIG. 1 of the attached drawings, which Figure is a transverse cutaway view of the eyeball (2).

As shown in FIG. 1, the eyeball is divided into two zones by a vascularized membrane (3) which is called the iris and of which the opening constitutes the pupil (10). In front of the iris there is a cavity which is closed at the front by a transparent membrane which is called the cornea (4). This cavity delimits the anterior chamber (5).

The anterior chamber (5) is limited at the back by the iris (3) which attaches into the ciliary body and separates, on the internal surface of the latter, two grooves: an anterior groove (6) called the ciliary band and limited at the front by the scleral spur (7), and a posterior groove (8), called the ciliary sulcus, and limited at the back by the ciliary processes (9) which are folds projecting from the choroid.

As shown in FIG. 1, the support of this implant (1), by means of its loops (12), should ideally be situated between the scleral spur (7) (to the rear of the latter in order to respect the filtering structures of the iridocorneal angle) and the root of the iris (3), that is to say as an anterior ciliary support.

The implant described according to Patent Application EP-A-0,195,881 incorporates a convergent lens, resulting in an optic part with thin edges, the peripheral thickness of which is of the same order as that of the loops for elastic support.

The solution proposed by that document appears impracticable for an implant incorporating a divergent lens intended, for example, to correct myopias and resulting, for this reason, in an optic part with thick edges, for the following reasons, it does not appear possible a priori to connect in an integral manner, that is to say retaining the material continuity of the implant, on the one hand the relatively thick edge of the optic part and on the other hand the relatively thin haptic part;

such a connection in any case constitutes a potential area of fragility of the implant;

it is not possible to increase the thickness of the haptic part, on the one hand if it is desired to retain all the flexibility required for the positioning of the implant and, on the other hand, by reason of the limited space available between the two ciliary bands of the eye.

Patent Application FR-A-2,603,186 has described and proposed an intraocular implant whose optic part comprises, on the one hand, a divergent lens having a flat anterior face and a concave posterior face and, on the other hand, a peripheral and annular zone having a convex and aspherical anterior face. The haptic part is separate and fitted on the optic part and comprises three suspension arms fixed on the abovementioned peripheral and annular zone; each arm is oriented at an acute angle relative to the tangent at the fixation point and comprises, at its free end, an element for anchoring in the anterior chamber.

This implant, although specific to a divergent lens, nevertheless has the following essential disadvantages:

a fitted haptic part does not permit centering of the implant in as safe and reliable a manner as an integral implant;

since the optic part is of large diameter and the peripheral edge of the optic part remains thick, this implant takes up a relatively large space in the anterior chamber; the risk of damaging the endothelium is thus greater;

the peripheral edge of the optic part remains relatively thick and thus, a priori, incompatible for the same reasons as above with an integral haptic part.

According to Patent FR-A-2,603,186 it should additionally be noted that the solution proposed leads to the existence, in the implant, of a peripheral annular zone, separate from the actual lens, ensuring the joining between the latter and the haptic part. The existence of this zone has disadvantages:

on the one hand, as regards the lens, it reduces the useful optic circular surface; whereas, it is important to have available a corrective lens which is as large as possible in relation to the maximum diameter of the iris;

on the other hand, this peripheral optic zone is often likely to transmit to the iris a secondary image, more or less blurred, in addition to that already transmitted by the actual lens.

SUMMARY OF THE INVENTION

The present invention relates to an intraocular implant of the first type described above, incorporating a divergent lens, retaining an integral structure between the optic and haptic parts, and maximizing the diameter of the useful optic zone.

According to the present invention, on the one hand the optic part is occupied substantially completely, that is to say is virtually identical with a divergent lens with thick edges, having an anterior face and a posterior face, both, for example, being concave; and, on the other hand, a connecting zone, of cross-section decreasing towards the free end of each loop, situated outside the optic part and attached to each elastic support loop, connects the latter to the optic part; each connecting zone has over its entire outer surface a curved profile, whatever the observation directions of the said zone.

The connecting zone defined above makes it possible to move from the thickness of the elastic support loops to the thickness of the thick edges of the optic part or lens, for example of the order of two to ten times greater than the first. With such a thickness ratio it is possible to vary the power of the divergent lens, for example between −10 and −70 diopters, while retaining the elasticity of the support loops of the implant.

In order to limit as far as possible the length of the connecting zone, the length of the latter does not exceed 10% of the total length of each elastic support loop. This makes it possible in particular to essentially preserve the elastic conformation of each support loop, without imparting excessive rigidity to the latter.

According to a preferred embodiment of the invention, the connecting zone has a hump arranged next to the anterior face of the lens at the point of departure of each loop for elastic support. Such a hump, with the corresponding inclination of the support loops, makes it possible, from the origin of the latter, to space the haptic part from the optic part and thus to limit as far as possible any secondary optic influence of the said haptic part.

BRIEF DESCRIPTION OF THE DRAWINGS

The present invention is now described with reference to the attached drawings in which.

DESCRIPTION OF THE PREFERRED EMBODIMENT

Figure 1:
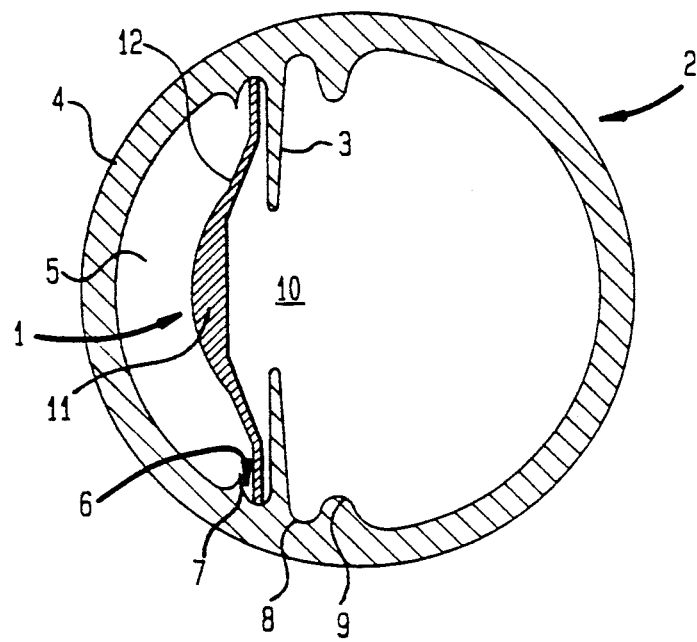
FIG. 1, as stated above, represents diagrammatically a cutaway view of an eye in which an implant according to the invention or according to the prior art has been implanted.

The intraocular implant shown in FIGS. 2 to 5 is designated by the general reference number (13). This implant is obtained by any suitable process in an integral manner, that is to say without discontinuity of material or components, from one end to the other. It is made of any appropriate transparent material, such as polymethylmethacrylate. It consists of an optic part (14) and a haptic part comprising two elastic loops for support (15).

In this example the optic part (14) is essentially identical to a biconcave divergent lens with a thick edge (16), of essentially circular shape, having a concave anterior face (17) and a concave posterior face (18).

The elastic loops for support extend on either side of the optic part (14), in the same diametral direction (50), from two points or zones of the optic part which are respectively and diametrically opposed.

Two connecting zones (19), arranged outside the optic part and situated on the two elastic support loops (15) respectively, connect the latter to the optic part and thus ensure the joining between the optic part and the haptic part of the implant. Each connecting zone (19) has a cross-section decreasing towards the free end (25) of each loop, going from the thickness (e) of the thick edge (16) of the optic part (14) to the nominal thickness of the loop (15), for example equal to (e/4), of circular transverse cross-section. The length of each connecting zone is as limited as possible and in general does not exceed 10% of the total length of each loop, from its point of departure on the optic part (14) to its free end (25). Each connecting zone (19) has a curved profile over its entire outer surface, although this is not shown completely in the Figures.

Figure 4:
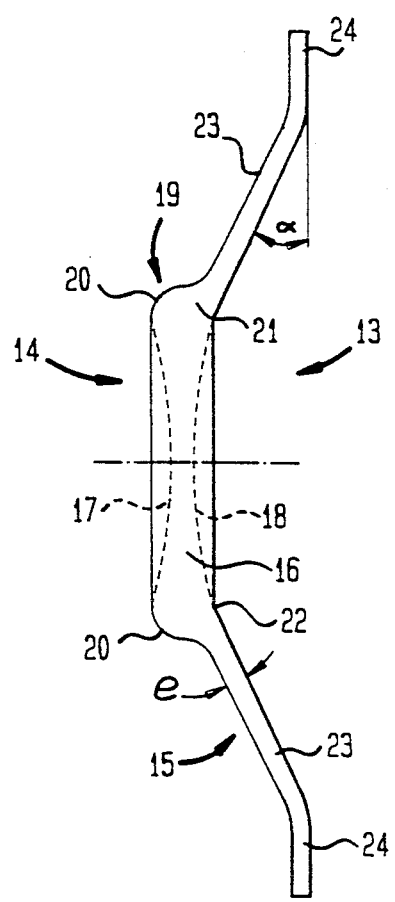
FIG. 4 is a side view of the first implant according to the invention.
Figure 5:
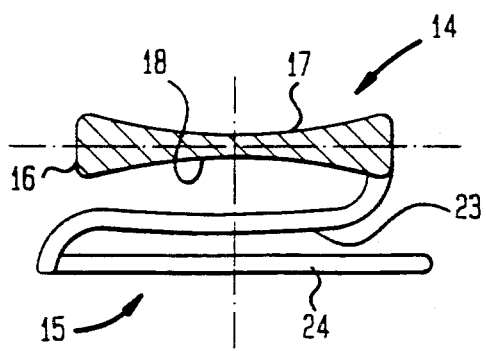
FIG. 5 is a transverse cutaway view, along the line V—V in FIG. 3, of the first implant according to the invention.

Each connecting zone (19) has a hump of rounded contour making it possible to go, over a short length, from the thick edge (16) of the optic part (14) to the loop (15). As shown in FIG. 4, this hump corresponds to a round.

Figure 2:
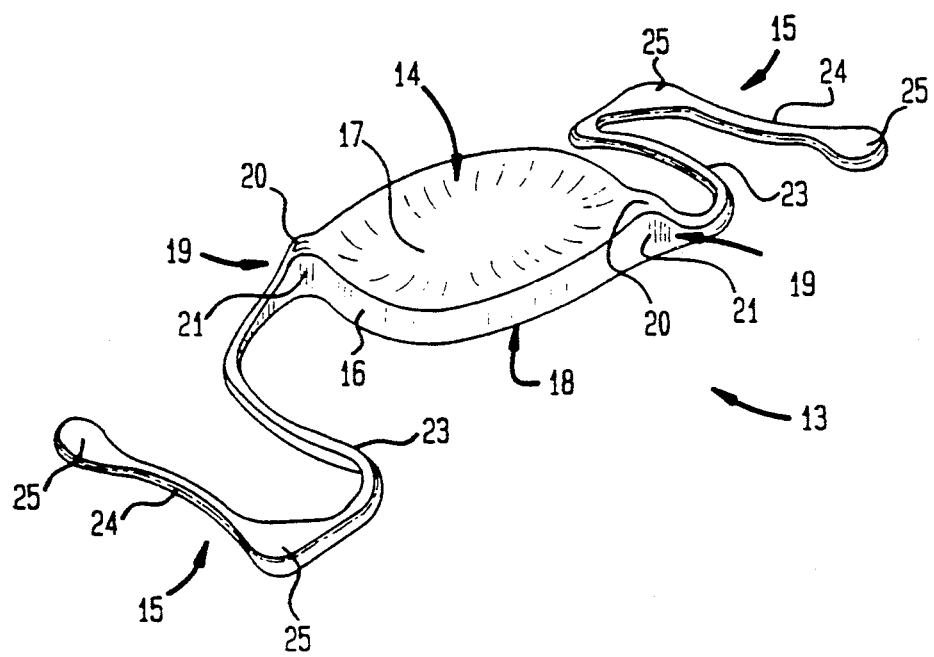
FIG. 2 shows a perspective view of a first implant according to the invention.
Figure 3:
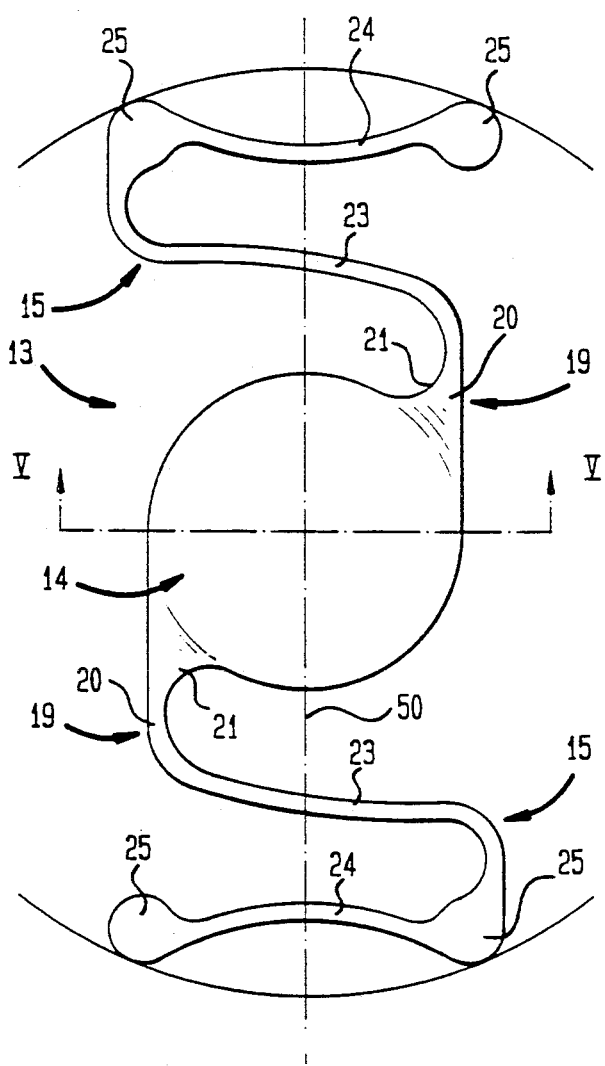
FIG. 3 is a front view of the first implant according to the invention.

As emerges from FIGS. 2 and 3, the flanks of the hump (20) consist of extensions of the thick edge (16) in the form of parts (21) curved in the direction away from the center of the biconcave lens (14). The hump (20) has an inside face (22) which is tangential to the posterior concave face (18) of the optic part (14).

Each loop (15) comprises continuously, and successively from its point of departure on the optic part (14), towards its free end (25), the connecting zone (19), a first part (23) curved in the arc of a circle, convex towards the outside of the lens (14), substantially orthogonal to the diametral direction (50) of extension of each loop (15), and a second part (24), curved and convex towards the inside of the lens (14), extending in the opposite direction to the first curved part (23), but substantially parallel to the latter.

Each second part (24) has at each of its two ends two areas (25) of rounded contour, each intended to constitute a point of support for the implant (13) in the ciliary band (6) of the anterior chamber (5) of the eye.

As emerges from FIG. 4, the first curved parts (23) of the support loops (15) are arranged approximately in a plane forming an acute angle α of the order of 25° to a plane containing the second curved parts (24) of the support loops (15), and parallel to the plane of the optic part (14).

According to this first embodiment, the intraocular implant (13) has sizes such that the diameter of the circle having as its center that of the optic part (14) and passing through the points most remote from the center of the areas (25) constituting the points of support for the implant (13), in other words the overall diameter, is equal to 13,000 micrometers + 250, the diameter of the optic part (14) is equal to 4,500 micrometers + 130, the thickness "e" of the loops (15) to 200 + 20 micrometers and the length of the second curved parts (24) of the loops (15) to 5,500 micrometers + 165. Such an intraocular implant (13) is produced by machining and then polishing the component material.

Of course, the thick-edged biconcave divergent lens constituting the optic part (14) can also be planoconcave. It permits correction of severe myopias and can have powers varying from −10 to −60 diopters depending on the radiuses of curvature of the anterior face (17) and posterior face (18) of the optic part (14).

The connecting zone (19) can connect the optic part (14) to various elastic support loops (15) of shapes different from that described hereinabove.

Thus, the two loops can each comprise a single convex part turned toward the optic part, these loops being curved interiorly in the same direction, following the direction of rotation of the hands of a watch.

The end part of each loop comprises a rounded support zone. By virtue of this arrangement of the loops, it is possible to arrange the implant by rotation during positioning in the eye.

What is claimed is:

1. Intraocular implant (13) for the anterior chamber of the eye, consisting of an optic part (14) comprising a lens of essentially circular shape, and a haptic part comprising two elastic loops (15) for support inside the eye, extending on either side of the optic part, in the same diametral direction (50), from two points of the optic part respectively and diametrically opposed, characterized in that the optic part (14) is substantially completely occupied by a divergent lens with thick edges (16), having an anterior face (17) and a posterior face (18), and a connecting zone (19) of cross-section decreasing towards the free end of each loop, situated outside the optic part, and fitted on each loop (15), connects the latter to the optic part, the said connecting zone having a curved profile over its entire outer surface, the optic part together with the elastic loops and each connecting zone being unitary and integrally formed of transparent material, the thick edge (16) of the optic part having a thickness twice to ten times greater than that of the loops (15) for elastic support.

2. An implant as claimed in claim 1, wherein each connecting zone (19) has a hump (20) arranged next to the anterior face (17) of the lens, at the point of departure of each loop (15) for elastic support.

3. An implant as claimed in claim 1, wherein the connecting zone (19) has a lower profile tangential to the posterior face (18) of the lens (14).

4. An implant as claimed in claim 1, wherein each loop (15) for elastic support comprises, continuously and successively from its point of departure on the optic part (14), towards its free end, a connecting zone (19), a first curved part (23), substantially orthogonal to the diametral direction (50) of extension of each said loop, and a second part (24) extending in the opposite direction to the said first curved part.

5. An implant as claimed in claim 4, wherein the second parts (24) of the two loops (15) for elastic support are each arranged in a posterior plane substantially parallel to the lens (14), next to its posterior face (18).

6. An implant as claimed in claim 5, wherein the first parts (23) of the two loops (15) for elastic support are each arranged in a plane forming an acute angle α to the posterior plane of the second parts (24).

7. An implant as claimed in claim 6, wherein the angle α is of the order 25°.

8. An implant as claimed in claim 1, wherein the length of the connecting zone (19) does not exceed 10% of the total length of each loop (15) for elastic support.

9. An intraocular implant (13) implantation into the anterior chamber of the eye, comprising:

an optic part (14) extending generally in a plane and consisting substantially entirely of a substantially circular divergent lens of $-10$ to $-70$ dioptres having a thick circumferential edge (16), an anterior face (17) and a posterior face (18), at least one of said anterior face (17) and said posterior face (18) being generally concave;

a pair of connecting zones (19) integral and unitary with said optic part (14), each said connecting zone (19) extending outwardly from said thick circumferential edge (16), said connecting zones (19) being spaced diametrically opposite one another, each said connecting zone (19) having a cross-section decreasing sharply from said circumferential edge (16) to a thin portion having a thickness from ½ to 1/10 the thickness of said circumferential edge (16), each said connecting zone further having a generally rounded hump extending from said circumferential edge (16) adjacent said concave anterior face (17), and each said connecting zone extending away from said circumferential edge (16) adjacent said posterior face (18) at an angle on the order of about 25° to the general plane of said optic part (14); and elastic support means for supporting said implant (13) within the eye comprising a pair of elastic loops (15) extending respectively from and unitary and integral with said thin portions of said connecting zones;

said implant (13 being formed of transparent plastic and said connecting zone (19) being no greater in length than 10% of the length of said elastic loops (15).

* * * * *